(12) United States Patent
Godfroid et al.

(10) Patent No.: US 9,253,996 B2
(45) Date of Patent: Feb. 9, 2016

(54) SUSTAINABLE CONVERSION OF CITRUS PEEL WASTE

(71) Applicants: Robert Godfroid, McKinney, TX (US); Deepali Palta, Dallas, TX (US); Sridevi Narayan-Sarathy, Frisco, TX (US); William B. Small, II, Crystal Lake, IL (US)

(72) Inventors: Robert Godfroid, McKinney, TX (US); Deepali Palta, Dallas, TX (US); Sridevi Narayan-Sarathy, Frisco, TX (US); William B. Small, II, Crystal Lake, IL (US)

(73) Assignee: Frito-Lay North America, Inc., Plano, TX (US)

( * ) Notice: Subject to any disclaimer, the term of this patent is extended or adjusted under 35 U.S.C. 154(b) by 0 days.

(21) Appl. No.: 13/660,254

(22) Filed: Oct. 25, 2012

(65) Prior Publication Data

US 2013/0109065 A1  May 2, 2013

Related U.S. Application Data

(60) Provisional application No. 61/551,722, filed on Oct. 26, 2011.

(51) Int. Cl.

| | |
|---|---|
| *C12P 5/02* | (2006.01) |
| *A23K 1/18* | (2006.01) |
| *C12P 7/62* | (2006.01) |
| *C12P 7/40* | (2006.01) |
| *C12P 7/08* | (2006.01) |
| *C08B 37/06* | (2006.01) |
| *B01D 11/02* | (2006.01) |
| *A23L 1/212* | (2006.01) |
| *C11B 9/02* | (2006.01) |
| *A23K 1/14* | (2006.01) |
| *C12P 7/10* | (2006.01) |

(52) U.S. Cl.
CPC ............... *A23L 1/2126* (2013.01); *A23K 1/146* (2013.01); *A23K 1/1813* (2013.01); *C11B 9/027* (2013.01); *C12P 5/023* (2013.01); *C12P 7/10* (2013.01); *C12P 7/625* (2013.01); *Y02E 50/16* (2013.01); *Y02E 50/343* (2013.01)

(58) Field of Classification Search
None
See application file for complete search history.

(56) References Cited

U.S. PATENT DOCUMENTS

| | | | | |
|---|---|---|---|---|
| 2,455,382 | A | * 12/1948 | Nelson | .............................. 536/2 |
| 3,819,737 | A | 6/1974 | Kubitz | |
| 5,567,462 | A | 10/1996 | Ehrlich | |
| 6,660,099 | B2 | 12/2003 | Antila | |
| 7,060,313 | B2 * | 6/2006 | Jones | ............................. 426/489 |
| 7,879,379 | B1 * | 2/2011 | Widmer et al. | ............... 426/481 |
| 8,017,171 | B2 | 9/2011 | Sample | |
| 2006/0177916 | A1 | 8/2006 | Stewart | |
| 2008/0213849 | A1 | 9/2008 | Stewart | |
| 2009/0110798 | A1 | 4/2009 | Gusek | |
| 2009/0291481 | A1 | 11/2009 | Hillyer | |
| 2010/0124583 | A1 | 5/2010 | Medoff | |

OTHER PUBLICATIONS

Hull, William Q; "Chemicals from Oragnes" Industrial and Chemical Engineering, 45, 876-890, 1953.*
Lopez, Jose Angel Siles, et al., "Biorefinery of waste orange peel," Critical Reviews in Biotechnology, 2010, 30(1), pp. 63-69 (7 pages).
Pourbafrani, Mohammad, et al., "Protective Effect of Encapsulation in Fermentation of Limonen-contained Media and Orange Peel Hydrolyzate," International Journal of Molecular Science 2007, 8, pp. 777-787 (11 pages).

* cited by examiner

*Primary Examiner* — Blaine Lankford
*Assistant Examiner* — David Berke-Schlessel
(74) *Attorney, Agent, or Firm* — Colin P. Cahoon; Celina M. Orr; Carstens & Cahoon, LLP

(57) ABSTRACT

A sustainable method and system for producing bio-fuels from citrus peels and the recovery of limonene and pectin prior to fermentation of the peel solids. In one embodiment a sustainable method and system for the concurrent recovery of limonene and pectin from citrus peels is disclosed. The peels are optionally zested, mixed with water and an acid, and then exploded in a jet cooker or a pressurized extruder. The exploded peels are transferred to a flash vessel where the remaining limonene and water vapor are separated into water and limonene. The pectin fraction is removed from the flash tank and extracted by centrifuge, precipitation and/or filtration. The remaining peel solids are fermented in an anaerobic digester which produces methane, ethanol, acids, $CO_2$ or other end products which can be used as fuel for power generation equipment sufficient to supply the processing system for sustainable operations as described herein.

15 Claims, 4 Drawing Sheets

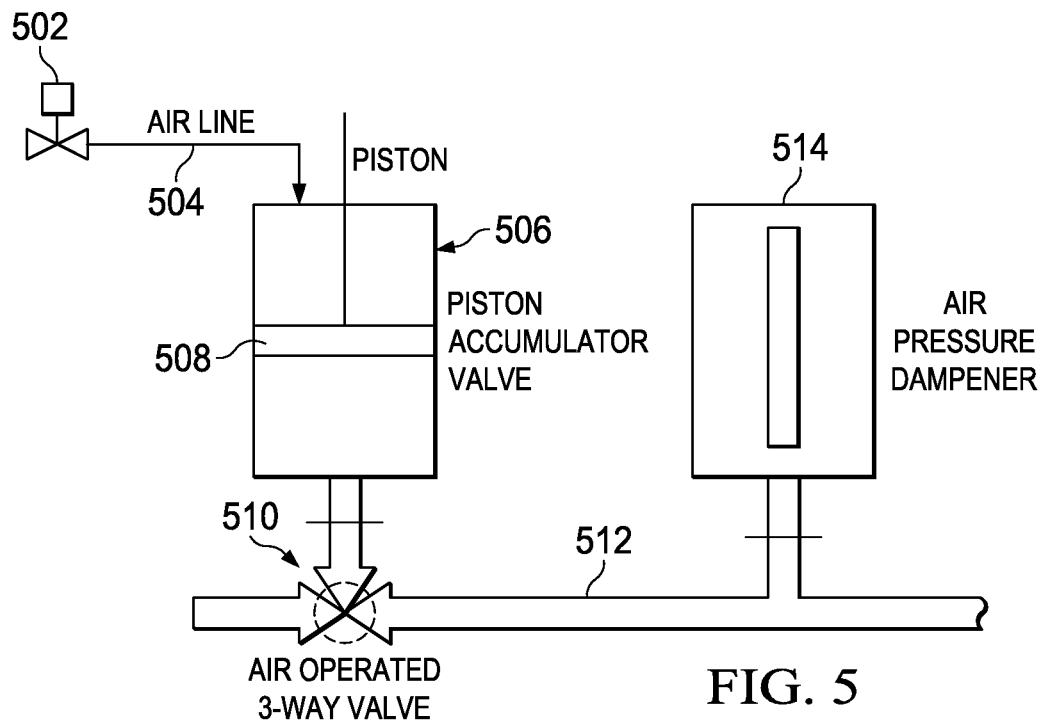
FIG. 5
FIG. 6
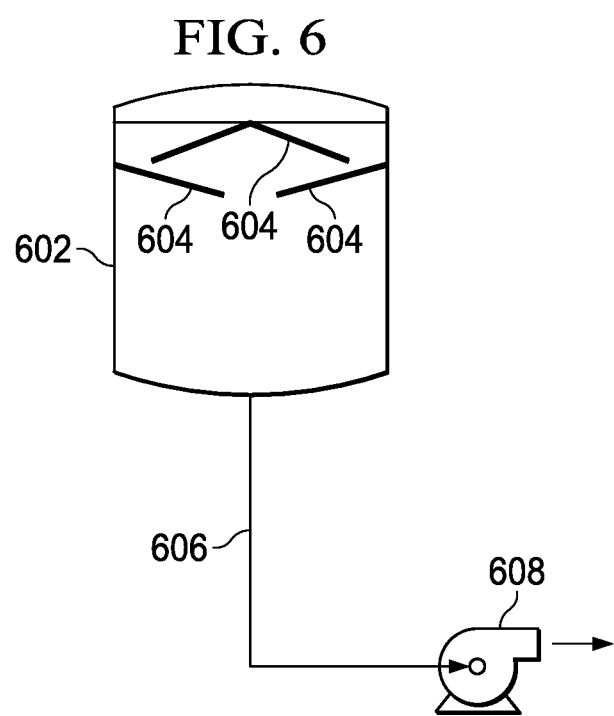

SUSTAINABLE CONVERSION OF CITRUS PEEL WASTE

CROSS-REFERENCE TO RELATED APPLICATION

This application claims the benefit of provisional U.S. Application No. 61/551,722 filed Oct. 26, 2011.

BACKGROUND OF THE INVENTION

1. Technical Field

The present invention relates to citrus peel waste processing and the recovery of high value material and chemicals. More specifically, the present invention relates to an improved sustainable method and system of processing citrus peels to remove limonene and pectin fractions thereby enhancing the remaining citrus peel solids for fermentation for the production of ethanol, valuable acids, methane and other recoverable high value chemicals resulting in a sustainable recovery method and system.

2. Description of Related Art

The generation of solid citrus peel waste presents a growing environmental and economic problem. Citrus peel waste consists mainly of citrus peels, membranes and seeds after the citrus fruit has been processed for the production of juices for consumption. It is estimated that approximately 5-7 billion pounds of citrus peel waste is produced annually from grapefruit and orange juice production operations in the State of Florida. Currently, the majority of this citrus peel waste is pressed and dried into cattle feed. At present prices, the large capital equipment and energy costs associated with the production and distribution of cattle feed from citrus peel waste are not recovered due to the low value of citrus waste as cattle feed and high cost of drying. Moreover, substantial amounts of essential citrus peel oil of d(+)-limonene are volatilized from the peel waste and often released into the atmosphere during peel drying operations in the feed production process. If the feed producer desires to recover this valuable limonene vapor fraction, they must install expensive vapor recovery systems to collect the limonene vapor.

Although citrus peel waste creates an environmental and waste disposal problem, it does contain substantial amounts of valuable chemical fractions such as soluble sugars and polymeric carbohydrates including pectin, cellulose and hemicellulose. These polymeric carbohydrates can be hydrolyzed to simple sugars by the use of acids or enzymes as known in the art. The resulting sugars may be fermented to ethanol, lactic acid or other products by known methods in the art.

One unique characteristic of citrus peels are that they contain a large amount of soluble sugars (e.g. glucose, fructose, galactose, arabinose and xylose) in solution within the tissues of the peels. By disrupting these tissues, the sugars can be released to increase the efficiency and speed of fermentation processes. Therefore, a need exists in the art for a process that effectively ruptures the citrus peel membrane to release the soluble sugars and other complex carbohydrates to improve the fermentation process at the highest concentrations possible. However, it is readily known that the presence of limonene in the citrus peel presents an obstacle to efficiently fermenting the citrus peels.

Limonene is a terpene contained within the peel of citrus fruits. Limonene is extremely toxic to fermenting microorganisms and its presence in the fruit peel provides a defense to mold and bacteria thereby naturally preventing microbial buildup and fermentation of the fruit. In processing peels into ethanol and/or other recoverable chemicals, it is desirable to remove a majority, if not all, of the limonene from the citrus peel prior to fermentation operations. For efficient fermentation, the limonene in the peel must be reduced below 3000 parts per million (ppm) and preferably below 1500 ppm as described and known in the art. Several methods of removing limonene from citrus peels are known such as cold pressing, supercritical $CO_2$ extraction, steam stripping, direct heating in a dryer with subsequent condensation of limonene, and solvent washing. These methods while effective are energy and chemical intensive, expensive and typically cost prohibitive. As such, a need exists for an economical and efficient method that extracts a substantial amount of limonene from the peel prior to fermentation to provide for the efficient production of methane, ethanol and/or other desired high value chemical products without contributing additional chemical byproducts and volume to the waste stream.

It is recognized by industry that citrus peel waste is an excellent source of pectin, limonene and other polysaccharides. Following removal of these constituents, the remaining peel solids can be fermented and converted into high value end products such as methane and ethanol and thus reduce the volume of peel waste and reduce subsequent disposal costs. Various steps for accomplishing the recovery of these products from citrus peels are known in the art such as processes utilizing steam injection and fermenting sugars into ethanol. Nonetheless, conventional citrus peel treatment is energy intensive resulting in considerable power expenses for operation. The prior art does not disclose a system integrating the inventive methods disclosed herein for addressing this large energy requirement. As such, a need exists in the art for a sustainable citrus peel processing method that improves the process efficiency for the removal of limonene and pectin prior to the fermentation of the peel into ethanol, methane and other recoverable chemicals that can be operated and fueled from the end products generated from fermenting citrus peels.

SUMMARY OF THE INVENTION

The invention disclosed herein presents a sustainable method and system for the recovery of limonene and pectin from citrus peels. In one embodiment, the citrus peels undergo particle size reduction and are then heated by steam injection and exploded in a pressure jet cooker at elevated temperature and pressure. The exploded peels are transferred to a flash vessel where the limonene and water vapor are vented to a condenser and separated into water and limonene. The substantially de-oiled peels are fermented in an anaerobic digester resulting in the production of biogas, acids and/or $CO_2$ products or the peel solids may be dried to produce animal feed products. Some of the resulting end products such as biogas, ethane, and methane may be used as fuels for power generation equipment to supply the citrus peel processing system for sustainable operations or used in the manufacture of high value products such as monomers and polymers.

In one embodiment, the invention disclosed herein presents a sustainable method and system for producing biofuels from citrus peels and the recovery of limonene and pectin prior to fermentation of the peels. In one embodiment, the zest is optionally substantially removed from the peels before or after juicing, then the peels are heated by steam injection in a jet cooker at elevated temperature and pressure. The heated peels are transferred to a flash vessel where the limonene and water vapor are vented to a condenser for separation into water and limonene. The remaining peel solids are fermented in an anaerobic digester resulting in the production of methane, $CO_2$, ethanol, or other fermentation products.

These products may then be used as fuel for power generation equipment sufficient to supply at minimum the processing system for sustainable operations.

In one embodiment, the invention herein presents a sustainable method and system for the concurrent recovery of limonene and pectin from citrus peels. The peels are optionally substantially zested and then mixed with an acid to reduce pH of the citrus peel slurry which is then heated in a jet cooker at elevated temperature and pressure by steam injection. The heated peels are transferred to a flash vessel where the limonene and water vapor are vented to a condenser and separated into water and limonene. The substantially de-oiled peel solids contain a high quality pectin fraction that is removed from the flash tank by washing with hot water and separated by centrifuge, precipitation and/or filtration. The remaining substantially pectin-free peel solids are then transferred and fermented in an anaerobic digester resulting in the production of methane, $CO_2$, ethanol, or other fermentation products. These end products may then be used as fuel for power generation equipment sufficient to supply the processing system for sustainable operations.

In one embodiment, the invention herein presents a sustainable method and system for the concurrent recovery of limonene and pectin from citrus peels. The peels undergo particle size reduction operations and are then mixed with water and an acid to reduce the pH of the citrus peel slurry. The citrus peels are then exploded in a jet cooker at elevated temperature and pressure by steam injection and transferred to a flash vessel where the limonene and water vapor fractions are vented to a condenser and separated into water and limonene. The high quality pectin fraction which has been de-oiled and solubilized is removed from the flash tank and separated from the remaining peel solids by centrifuge and recovered by precipitation, filtration and/or membrane separation techniques. The remaining de-oiled peel solids are then transferred to an anaerobic digester for fermentation resulting in the production of biogas, acids including but not limited to acetic, lactic, succinic and butyric acids, and $CO_2$ products or dried to produce animal feed products. Some of the resulting end products such as biogas may be used as fuel for power generation equipment to supply the citrus peel processing system for sustainable operations or used in the manufacture of high value products such as monomers and polymers.

In one embodiment, the invention herein presents a method and system for the recovery of limonene and pectin from citrus peel waste with the ethanol and sugar production streams from the pectin recovery operation being utilized as additional fuel for the fermentation processing of the peel waste. The zest is optionally substantially removed from the citrus peels, the citrus peels are mixed with an acid and water to reduce pH of the citrus peel slurry, and then the citrus peel slurry is heated in a jet cooker at elevated temperature and pressure by steam injection. The limonene-water vapor is vented to a condenser for separation into water and limonene. The remaining peel solids are then mixed with water and separated by a first centrifuge to extract a soluble pectin fraction. The pectin solution fraction is then evaporated, precipitated with a precipitant such as ethanol and filtered by rotary filtration or membrane separation resulting in the separation of wet pectin from the ethanol and soluble sugars fraction. The high quality pectin fraction is then dried and removed for further processing. The ethanol stream is separated by distillation then recycled in the system to further facilitate precipitation. The sugar stream is sent to anaerobic digestion for fermentation. An optional second separator, such as a centrifuge, dewaters the de-oiled citrus peel solids which are transferred to a fermentation unit for anaerobic digestion to produce methane, $CO_2$, ethanol, acids or other fermentation by-products. These end products may then be used as fuel for power generation equipment sufficient to supply the citrus peel processing system for sustainable operations.

In one embodiment, the invention herein presents a method and system for the recovery of limonene and pectin from citrus peels with the sugar production stream from the pectin recovery operation being utilized as an additional medium along with the de-oiled citrus peels for fermentation. The citrus peels undergo particle size reduction operations and are then mixed with water and an acid to reduce the pH of the citrus peel slurry. The citrus peels are exploded in a jet cooker at elevated temperature and pressure by steam injection and then transferred to a flash vessel where the limonene and water are vented to a condenser and separated into water and limonene fractions. The remaining high-quality pectin fraction that has now been substantially de-oiled and solubilized is removed from the flash tank and separated from the peel solids by a separation equipment, such as a centrifuge, and recovered by precipitation, filtration and/or membrane separation techniques. The remaining de-oiled peel solids are then fermented in an anaerobic digester resulting in the production of biogas, ethanol, acids and $CO_2$ products or dried to produce animal feed products. Some of the resulting end products such as biogas may be used as fuel for power generation equipment to supply the citrus peel processing system for sustainable operations or used in the manufacture of high value products such as monomers and polymers.

Other aspects, embodiments and features of the invention will become apparent from the following detailed description of the invention when considered in conjunction with the accompanying figures. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

BRIEF DESCRIPTION OF THE FIGURES

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying figures, wherein:

FIG. 5 is a schematic drawing of an expansion/explosion valve integrated with the recovery system disclosed herein; and FIG. 6 is a schematic drawing of a flash tank with vapor baffles integrated with the recovery system disclosed herein.

DETAILED DESCRIPTION

Figure 1:
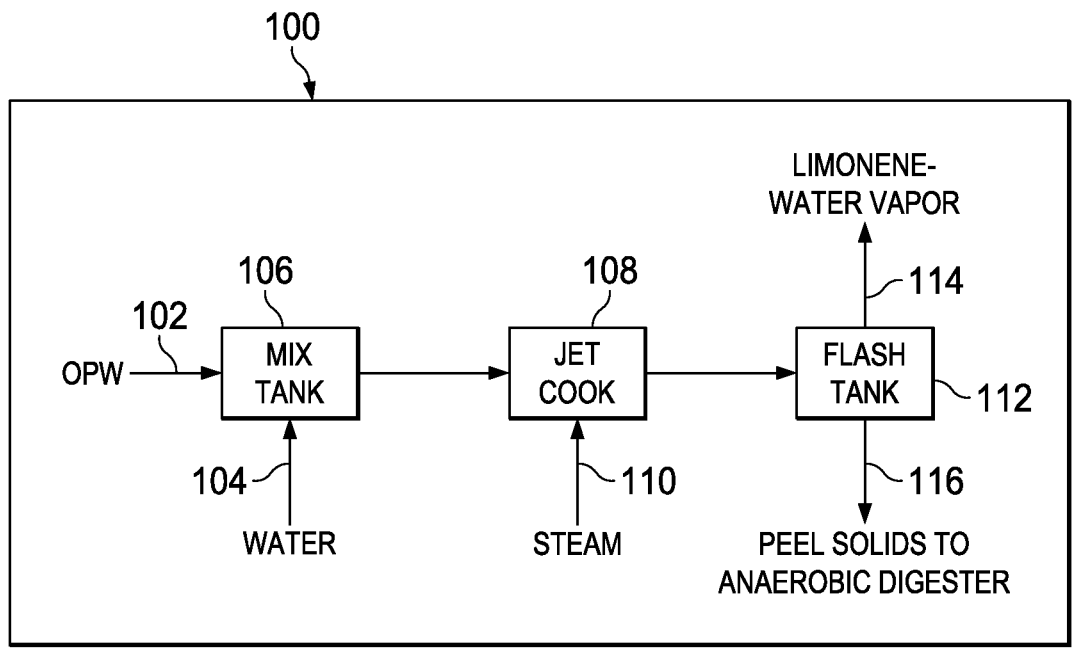
FIG. 1 is a block diagram showing an embodiment of the limonene removal process of the invention disclosed herein.

FIG. 1 depicts a block diagram of an embodiment of the limonene removal process 100 according to the invention disclosed herein. In one embodiment, a significant volume of the citrus peels have been significantly dewatered by pressing after juicing operations by means as known in the art. In one embodiment, pressing is accomplished using a hammer mill. Pressing increases the total solids content for the citrus peels to make anaerobic digestion more efficient. A higher total solids content reduces the volume of peel waste received by the anaerobic digestion reactor and thereby could reduce the size of the reactor required from implementation of the invention disclosed herein. Pressed peel waste (i.e. lower moisture content of less than ~65%) is typically used for ensiling processes (pickling of orange peels). Ensiling processes are utilized to prepare and store orange peel waste for off-season digestion.

As shown in FIG. 1, citrus peels or orange peel waste (OPW) 102 are mixed with water 104 in mix tank 106 to condition the pH of the resulting mixture to between about 4.0 and 5.0, and more preferably to about 4.7. The resulting citrus peel mixture in mix tank 106 is then transferred to a pressure cook vessel 108 (also referred to herein as a "jet cooker") where the conditioned citrus peel mixture is rapidly heated under elevated temperature and pressure. In one embodiment, the citrus peel mixture is heated by the injection of steam 110 into the jet cooker 108 elevating the temperature of the citrus peel mixture to temperatures between about 100 to 130 degrees Celsius under a pressure of between about 10 to 30 psig and more preferably to about 120 degrees Celsius at between about 15 to 20 psig. The citrus peel mixture is contained and maintained at elevated temperature and pressure within pressure cook vessel 108 until the desired set temperature is reached. The pressure may be maintained by adjustable pressure valve(s) and/or an expansion/explosion valve as later described herein and by maintaining the pressure head in a vertical column arrangement according to elevation. The heated peels are then exploded into a flash tank 112 maintained at reduced or atmospheric pressure resulting in the release of a substantial portion of the limonene fraction and water fraction by volatilization to a vapor phase. In one embodiment, an "expansion/explosion" valve (which is further described and shown in FIGS. 5 and 6) operates to open to the flash tank 112 where the hot citrus peel mixture is transferred at reduced or atmospheric pressure resulting in the release of the limonene and a part of the water from the citrus peels by volatilization to a vapor phase. The limonene oil-water vapor is vented from flash tank 112 and separated by a condenser or other means as is known in the art. The remaining de-oiled citrus peel solids which have settled in the flash tank 112 are removed for conversion to other high value products, or as depicted in FIG. 1, transferred to a fermentation unit 116, which in the depicted embodiment comprises an anaerobic digester, for the recovery of bio-gas such as methane, bio-fuels such as ethanol, and other high value chemical products.

Figure 2:
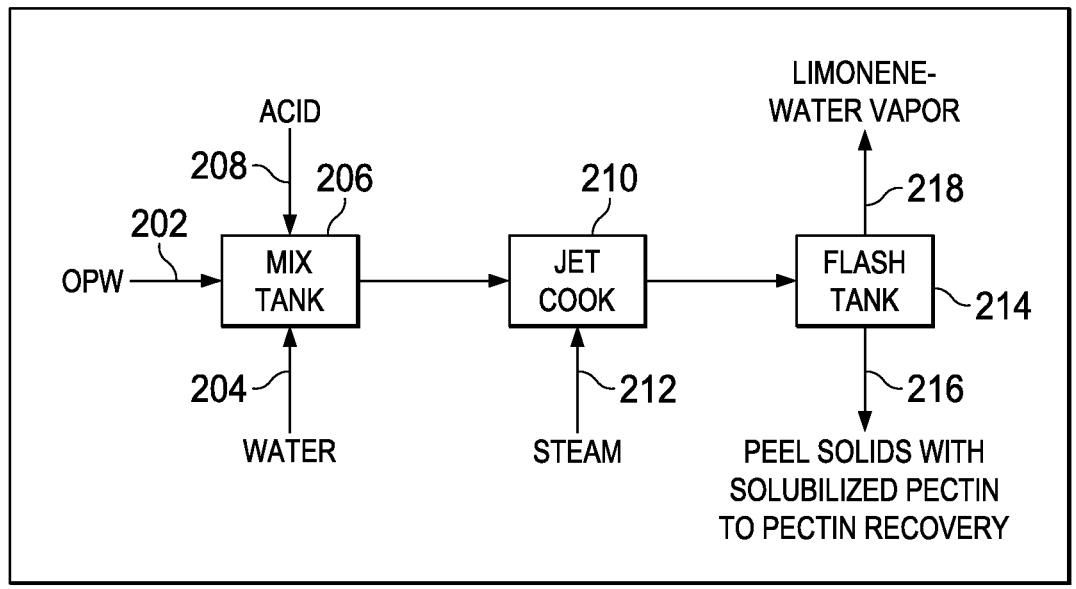
FIG. 2 is a block diagram depicting an embodiment of the limonene and pectin removal process of the invention disclosed herein.

In one embodiment, prior to being introduced into the mix tank 106 as shown in FIGS. 1 and 2, the citrus peels are optionally zested. The term "zest" refers to the grated citrus rind material formed by the removal of a substantial portion of the colored outer skin or "rind" of the citrus peel which contains a majority of the limonene fraction immobilized in the peel. Removal of the outer skin or citrus peel rind, also referred to herein as "zesting," may be accomplished by mechanical and/or chemical methods as known in the art. By zesting the citrus peels prior to introducing the citrus peels 102 into the mix tank 106, a large portion of the limonene fraction is removed while still contained within the peel rind therefore reducing the apparatus and energy requirement necessary for removal of the limonene from the flash tank 112 as described in one embodiment herein or by other recovery processes as known in the art. The citrus peel zest may then be transported to a limonene recovery facility for further treatment. Additionally, the step of zesting the citrus peel waste may be performed prior or concurrently with any of the pretreatment and/or treatment processes depicted in FIGS. 1, 2, 3 and 4 and as further described and shown herein.

Referring to FIG. 2, one embodiment of the invention disclosed herein is shown wherein limonene and pectin fractions contained within the citrus peel are recovered concurrently. Pressed citrus peels 202 are mixed with water 204 in mix tank 206 to form a citrus peel slurry. A concentrated acid 208, in one embodiment concentrated phosphoric acid, is mixed with the citrus peel slurry in order to condition the pH of the resulting mixture to between about 1.0 and about 3.0, and more preferably to about 2.0. Other acids which may be used to condition the pH of the citrus peel slurry include hydrochloric acid, sulfuric acid, and nitric acid among others as is known in the art. The resulting citrus peel slurry in mix tank 206 is then transferred to a pressure cook vessel 210 where the conditioned citrus peel slurry is rapidly heated under elevated temperature and pressure. In one embodiment, the citrus peel slurry is heated by the injection of steam 212 into the jet cooker 210 elevating the temperature of the citrus peel slurry to temperatures between about 100 to about 130 degrees Celsius under a pressure of between about 10 to about 30 psig and more preferably to about 120 degrees Celsius at between about 15 to about 20 psig. The citrus peel slurry is contained and maintained at elevated temperature and pressure within pressure cook vessel 210 for a period of about 5 seconds to about 11 minutes. As previously described, the rapid heating of the citrus peel "explodes" the peel such that limonene oil-water vapor is released from the citrus peels. The extended hold time of citrus peels in the jet cooker 210 enhances the solubility of the pectin in the citrus peel. The steam extraction process in the presence of acid increases the solubilization of pectin in water. This increased solubilization increases the separation efficiency of pectin from other carbohydrates like cellulose present in citrus peels. While this can be accomplished after instantaneous heating, better yields can be achieved with cooking times of up to about eleven minutes. The hot citrus peels and limonene oil-water vapor are transferred to a flash tank 214 where the limonene oil—water vapor 218 fraction is vented to a lower pressure or atmospheric pressure and removed and separated downstream by a condenser or other separation means as is known in the art. The remaining de-oiled citrus peel solids with solubilized pectin 216 are transferred to a pectin recovery unit for removal of the pectin fraction by means and processes as is known in the art. The remaining citrus peel solids may then be transferred to a sacchrification and/or fermentation system for recovery of end products as is known in the art.

In one embodiment of the invention disclosed herein, the pressure cook vessel 210 includes an extruder mechanism whereby the citrus peels are further ground into smaller particle sizes while being heated under elevated pressure as previously described. By conducting the extrusion and flash heating processes concurrently, the recovery efficiency of the disclosed process is greatly enhanced. Extruders commonly used in the cooking of agricultural products, such as corn meal, are suitable to this application. These can be single or double barrel extruders. Typically these extruders add heat via mechanical work on the peel waste, and or via steam or electrical heating on the extruder barrel. Heat can also be added by injection of steam into the extruder barrel. Pressure is added to the peel waste slurry via the action of the extruder against the exit orifice, addition of pressurized steam, or via electrical or steam heating of the extruder barrel.

Figure 3:
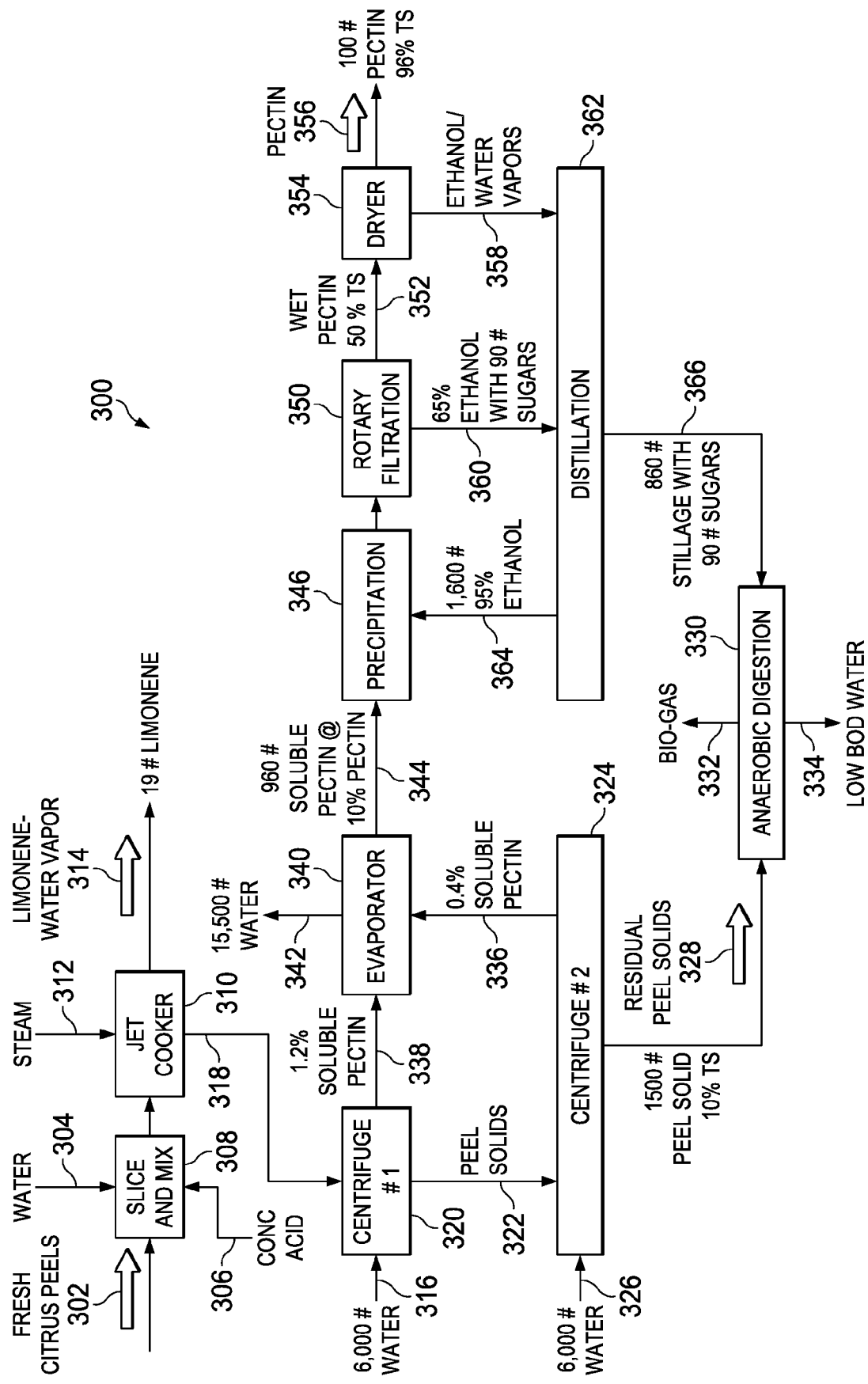
FIG. 3 is a block diagram illustrating an embodiment of the sustainable limonene and pectin removal process integrated with the fermentation process for producing biofuels and other high value chemicals of the invention disclosed herein.

With reference to FIG. 3, an example embodiment of the invention disclosed herein is depicted in further detail. Citrus peels 302 are mixed with water 304 and an acid 306, such as concentrated phosphoric acid, in mix tank 308 conditioning the citrus peel slurry in mix tank 308 to a pH of about 1 to about 5, and more preferably to a pH of about 2.0. The citrus peel slurry is transferred to jet cooker vessel 310 and rapidly heated by the injection of steam 312 into the jet cooker vessel 310 to a temperature of about 110 to about 180 degrees Celsius, more preferably to about 120 degrees Celsius, under an elevated pressure of about 10 to about 100 psig, more preferably about 15 to about 20 psig, for about 0 to about 30 minutes, and more preferably about 10 to about 20 minutes. The limonene oil-water vapor fraction 314 released by the flash heating process is removed, condensed and separated by other means as is known in the art.

The remaining heated citrus peel solids 318 are transferred from jet cooker vessel 310 and mixed with water 316 in first centrifuge 320 where the citrus peel slurry is separated into peel solids 322 and soluble pectin 338. The peel solids 322 are transferred to second centrifuge 324 and mixed with water 326. After separation by second centrifuge 324 for additional dewatering and pectin recovery, the residual peel solids 328 are sent to a fermentation reactor 330 which in the depicted embodiment comprises an anaerobic digester. In one embodiment, remaining citrus peel solids 318 are sent to the fermentation reactor 330 without undergoing first and/or second rounds of separation by centrifugation. During anaerobic fermentation processes conducted within fermentation reactor 330, citrus peel solids are digested to produce high value chemicals, polyhydroxylalkanoate, biogas, methane, ethanol and/or acids, such as acetic and lactic acid.

In one embodiment, jet cooker vessel 310 is replaced with a heated extruder for purposes of accomplishing the pressure-cooking process as described herein. Extrusion processes developed for the pre-treatment of ligno-cellulosic material in cellulosic ethanol production are suitable for this purpose Twin screw extruders have been utilized at low temperatures, such as about 50 degrees Celsius, in the presence of chemical additives such as sodium hydroxide and such processes could be modified for purposes of creating an extrusion steam explosion system at elevated temperatures, such as about 120 degrees Celsius, to pretreat the citrus peel waste for the purposes described herein.

In one embodiment after separation by first centrifuge 320, recovered soluble pectin 338 is transferred from first centrifuge 320 to evaporator 340. The pectin solution volume is reduced in evaporator 340 to produce a more concentrated pectin solution 344. Water 342 from this reduction is drawn off and transferred to a tank (not shown) for further processing or disposal. The substantially reduced and/or concentrated pectin 344 is routed to a precipitation unit 346 where it is mixed with a precipitating agent 364, such as ethanol or isopropanol, by direct injection or from downstream processing operations as depicted. In the depicted example embodiment, ethanol serves to precipitate pectin from the concentrated solution as pectin is not soluble in ethanol. The sugars remain soluble allowing removal of pectin from solution. In one embodiment, about 90% ethanol is used for pectin precipitation.

In the example embodiment shown in FIG. 3, about 800 lbs. of ethanol is added to precipitate 500 lbs. of 8% pectin solution. The slurry of solid pectin, ethanol soluble sugar and water is then transferred to a rotary filtration unit 350 for separation of the solid pectin. After separation by rotary filtration unit 350, the resulting wet pectin 352 is transferred to a dryer 354 where dried pectin 356 is then removed. The remaining ethanol/water vapor fraction 358 is routed to distillation unit 362. Concurrently during rotary filtration 350, ethanol and water with soluble sugars 360 are recovered and directed to distillation unit 362. The streams produced after centrifugation by second centrifuge 324 and distillation unit 362 are then transferred to fermentation reactor 330 where the resulting mixture of residual peel solids 328 and stillage 366 undergo anaerobic fermentation processes resulting in the recovery of bio-gas 332 and low biological oxygen demand (BOD) water 334. Biogas 332 may then be removed and stored for use in power generation of the process equipment described herein resulting in a sustainable method and system for converting citrus peels or placed into a pipeline for sale on the gas market. In general terms, low BOD water is an indicator that little to no pollutants are present in the effluent water and that there is very little aerobic bacterial activity which indicates good water quality. Low BOD water 334 is then removed and stored in a tank for further use or processing within the treatment system described herein or, if within environmental discharge limits, released for aquifer recharge or sold as irrigation water.

In one embodiment, the solubilized pectin is recovered by membrane separation techniques in order to avoid the use of alcohol for pectin precipitation. Using an ultrafiltration membrane unit, the removal of a substantial portion of water and sugars is accomplished as the concentration of sugar on the concentrate side of the membrane would remain relatively constant, while the pectin concentration increases incrementally to a maximum concentrate percentage. After separation occurs, spray drying processes may be utilized to recover the pectin cake for further processing.

Figure 4:
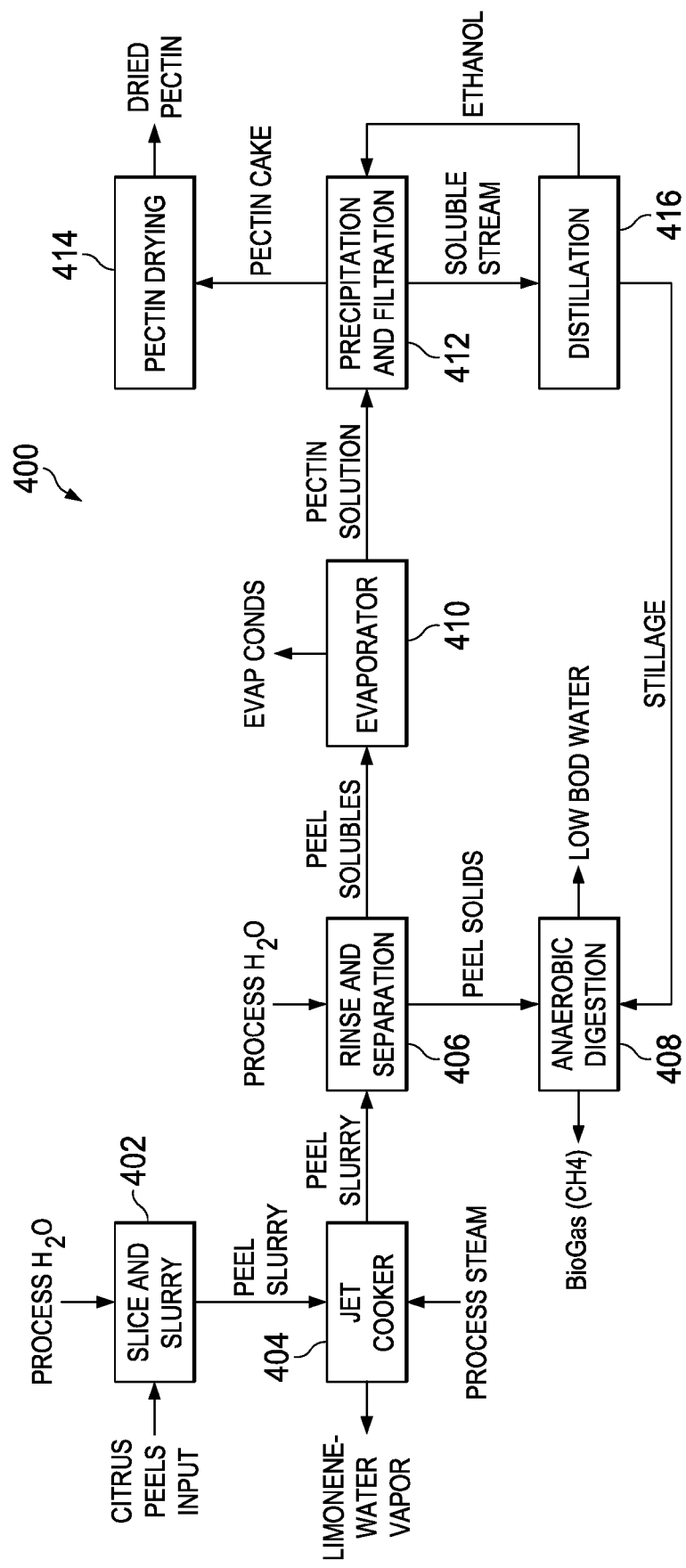
FIG. 4 is a block diagram illustrating an embodiment of the sustainable limonene and pectin removal process integrated with the fermentation process for producing biofuels and other high value chemicals of the invention disclosed herein.

Turning to FIG. 4, one example embodiment of the invention disclosed herein is depicted in further detail wherein orange citrus peels are used as the citrus peel feedstock. At Step 402, orange citrus peels are sliced and mixed with process water to form a peel slurry. At Step 404, the peel slurry is transferred to a jet cooker vessel where it is steam heated and the resulting limonene and water vapor extracted from the peel slurry is recovered and removed from the jet cooker vessel. The peel slurry is then transferred to a rinse and separation unit at Step 406 where the peel slurry is rinsed with process water and the peel solids separated from peel solubles by centrifugation or other separation means as known in the art. At Step 408, the peel solids are transferred to an anaerobic digester where biogas is produced and recovered as a result of fermentation processes. Low BOD water is recovered and removed for further processing and/or disposal. At Step 410, the peel waste solubles are transferred to an evaporator where moisture is substantially removed and substantially drying occurs in the remaining pectin fraction. The evaporated condensate is removed and the remaining pectin fraction transferred to a precipitation and filtration unit. At Step 412, the pectin solution is further precipitated and filtered resulting in a pectin cake which is removed for drying at Step 414. The dried pectin is then removed for further processing and use as is known in the art. The soluble waste stream remaining after the precipitation and filtration step is transferred to a distillation unit where ethanol is recovered as a by-product of the distillation process at Step 416. The remaining stillage is transferred to the anaerobic digester for fermentation and the recovery of biogas and low BOD water as shown. While the foregoing embodiment recites orange peels as the feedstock, other citrus peel feedstock may be utilized such as lime peels and lemon peels among other citrus fruits. The recitation of orange peels or orange peel waste is not to be construed as the limited feedstock in which any of the inventive embodiments disclosed herein may be applied.

FIG. 5 is a depiction of the expansion/explosion valve apparatus which is situated between the jet cooker 210 and flash vessel 214 in one embodiment of the invention described herein. A compressed air source (not shown) delivers pressurized air via valve 502 in fluid communication with air line 504 into a chamber of piston accumulator valve 506. Piston accumulator valve 506 comprises a valve body with an air piston 508 secured therein. Piston 508 acts to increase or decrease the pressure existing in air line 512 which is in fluid communication with three way air valve 510. Air pressure dampener 514 acts to dampen the pressure in air line 512 between the jet cooker 210 and flash vessel 214 (see FIG. 2) to maintain the pressure in the line 512 at the desired set point for peel explosion to take place and to maintain and to reduce the pressure in the jet cooker 210 as the limonene and water vapor are vented to the flash vessel 214,602 (see FIG. 6) as a result of the actuation of the piston accumulator valve 506.

FIG. 6 is a depiction of a flash vessel 602 with integrated baffles 604 which act to reduce the carryover of solids to the condenser or condensate vessel (not shown). Baffles 604 allow the vapor to rise and separate from the peel solids residing in the flash vessel 602. As the limonene oil and water vapor fractions are then vented from the flash vessel 602, baffles 604 prevent the peel solids from exiting the flash vessel 602 during the venting process. The limonene and water vapor fractions are then separated by a condenser as is known in the art. In one embodiment, the remaining substantially de-oiled citrus peel solids which have settled to the bottom of flash vessel 602 may be immediately removed from the flash vessel 602 via pump 608 which is in fluid communication with flash vessel 602 via piping 606 for landfilling, fermentation, biological digestion or treatment via other recovery processes, or dried for animal feed products. In one embodiment, the peel solids are transferred from flash vessel 602 to a fermentation unit, such as an anaerobic digester, for the recovery of bio-gas, methane, ethanol or other high value chemicals.

Unless otherwise noted, the citrus peels are processed through the systems by transport means as is known in the citrus peel processing industry. For example, conveying systems such as a belt system or piping systems may readily convey the citrus peel solids between processes. Pumping means such as pumps equipped to pump liquid and solids matter in piping may be integrated within the system to transport mixed phase materials between the processing stations described herein. Heating means may comprise steam, hot gases, heated conveyors/agitators/extruders or other heating means as are known in the art to provide the heat necessary for practicing the system and method disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

While the invention has been particularly shown and described with reference to a preferred embodiment, it will be understood by those skilled in the art that various changes in form and detail may be made therein without departing from the spirit and scope of the invention.

Additional Description

The following clauses are offered as further description of the disclosed invention.

1. A method, comprising:
reducing the particle size of a citrus peel feedstock;
mixing the citrus peels with water to form a citrus peel slurry in a mixing feed tank;
heating the citrus peel slurry in the mixing feed tank;
pumping the heated citrus peel slurry to a jet cooker;
exposing the citrus peel slurry in the jet cooker to pressurized steam to substantially elevate the temperature of the citrus peel slurry resulting in the formation of a vapor containing limonene oil and water;
venting the vapor containing limonene oil and water to an unpressurized flash vessel which operates to separate the limonene oil and water vapor from the citrus peel slurry;
condensing the limonene oil and water vapor in a condensate vessel where the limonene oil and water vapor are separated; and,
recovering the substantially de-oiled citrus peel solids.

2. The method according to any preceding clause wherein the citrus peels are substantially pressed before they are mixed with water to from a citrus peel slurry.

3. The method according to any preceding clause wherein the citrus peels are substantially zested before they are mixed with water to form a citrus peel slurry.

4. The method according to any preceding clause wherein the citrus peels are pre-heated to a temperature of about 35 to about 70 degrees Celsius.

5. The method according to any preceding clause wherein the citrus peel slurry is heated with steam to about 100 to about 135 degrees Celsius.

6. The method according to any preceding clause wherein the citrus peel slurry is heated under a pressure of about 10 psig to about 100 psig.

7. The method according to any preceding clause further comprising fermenting the substantially de-oiled citrus peels in an anaerobic digester to produce methane gas.

8. The method according to any preceding clause further comprising fermenting the substantially de-oiled citrus peels in an anaerobic digester to produce acids.

9. The method according to any preceding clause further comprising fermenting the substantially de-oiled citrus peels in an anaerobic digester to produce polyhydroxylalkanoate.

10. The method according to any preceding clause wherein the substantially de-oiled citrus peels are substantially dried for animal feed.

11. The method according to any preceding clause wherein the substantially de-oiled citrus peels are substantially hydrolyzed and fermented to produce ethanol.

12. A method, comprising:
reducing the particle size of a citrus peel feedstock;
mixing the citrus peels with water to form a citrus peel slurry;

adjusting the pH of the citrus peel slurry with an acid in a mixing feed tank;
heating the citrus peel slurry in the mixing feed tank;
pumping the heated citrus peel slurry to a jet cooker;
exposing the citrus peel slurry in the jet cooker to pressurized steam to substantially elevate the temperature of the citrus peel slurry resulting in the formation of a vapor containing a limonene and water fraction, a solubilized pectin liquor fraction, and a substantially de-oiled citrus peels fraction;
separating the substantially solubilized pectin fraction from the substantially de-oiled citrus peel fraction; and,
recovering a substantial amount of pectin from the solubilized pectin liquor.

13. The method according to clause 12 further comprising venting the vapor containing limonene oil and water to an unpressurized flash vessel.

14. The method according to clause 13 further comprising separating the limonene oil and water fractions from the vapor in a condensate tank.

15. The method according to clauses 12-14 wherein the citrus peels are substantially pressed before they are mixed with water to from a citrus peel slurry.

16. The method according to clauses 12-15 wherein the citrus peels are substantially zested before they are mixed with water to form a citrus peel slurry.

17. The method according to clauses 12-16 wherein the citrus peel feedstock is substantially rinsed prior to being exposed to pressurized steam.

18. The method according to clauses 12-17 wherein the citrus peels are pre-heated to a temperature of about 35 to about 70 degrees Celsius.

19. The method according to clauses 12-18 wherein the citrus peel slurry is heated with steam to about 100 to about 135 degrees Celsius.

20. The method according to clauses 12-19 wherein the citrus peel slurry is heated under a pressure of about 10 psig to about 100 psig.

21. The method according to clauses 12-20 wherein the citrus peel slurry residence time within the jet cooker is from about one to about twenty minutes.

22. The method according to clauses 12-21 wherein a substantial portion of solubilized pectin is separated from the citrus peel solids by a centrifuge.

23. The method according to clauses 12-22 wherein a substantial portion of solubilized pectin is concentrated in an evaporator.

24. The method according to clauses 1223 wherein a substantial portion of pectin is recovered from solubilized pectin liquor by precipitation.

25. The method according to clauses 12-24 wherein a substantial portion of pectin is recovered from solubilized pectin liquor by membrane separation.

26. The method according to clause 25 wherein the recovered pectin is further substantially spray dried.

27. The method according to clauses 12-26 wherein the substantially de-oiled citrus peels are anaerobically digested to produce biogas.

28. The method according to clauses 12-27 wherein the substantially de-oiled citrus peels are anaerobically fermented to produce acids.

29. The method according to clauses 12-28 wherein the substantially de-oiled citrus peels are fermented to produce polyhydroxylalkanoate.

30. The method according to clauses 12-29 wherein the substantially de-oiled citrus peels are substantially hydrolyzed and fermented to produce ethanol.

31. The method according to clauses 12-30 wherein the substantially de-oiled citrus peels are substantially dried for animal feed.

We claim:

1. A method of recovering pectin from citrus peels comprising:
removing the zest from the citrus peels;
mixing the citrus peel with water to form a citrus peel slurry;
adjusting the pH of the citrus peel slurry with an acid in a mixing feed tank;
heating the citrus peel slurry in the mixing feed tank;
pumping the heated citrus peel slurry to a pressure cook vessel;
exposing the citrus peel slurry in the pressure cook vessel to pressurized steam to substantially elevate the temperature of the citrus peel slurry resulting in the formation of a vapor containing a limonene fraction and a water fraction, a solubilized pectin liquor fraction, and a substantially de-oiled citrus peel fraction, wherein the citrus peel slurry residence time within the pressure cook vessel is from about one to about twenty minutes;
separating the substantially solubilized pectin fraction from the substantially de-oiled citrus peel fraction prior to any fermentation, hydrolyzation, digestion or drying of the substantially de-oiled citrus peel fraction; and,
recovering a substantial amount of pectin from the solubilized pectin liquor.

2. The method of claim 1 further comprising venting the vapor containing limonene oil and water to an unpressurized flash vessel.

3. The method of claim 2 further comprising separating the limonene oil and water fractions from the vapor in a condensate tank.

4. The method of claim 1 wherein the citrus peel feedstock is substantially rinsed prior to being exposed to pressurized steam.

5. The method of claim 1 wherein the citrus peels are preheated to a temperature of about 35 to about 70 degrees Celsius.

6. The method of claim 1 wherein the citrus peel slurry is heated with steam to a temperature of about 100 to about 135 degrees Celsius.

7. The method of claim 1 wherein the citrus peel slurry is heated under pressure of about 10 psig to about 100 psig.

8. The method of claim 1 wherein the citrus peel slurry residence time within the pressure cook vessel is up to about 11 minutes.

9. The method of claim 1 wherein the substantially de-oiled citrus peels are anaerobically fermented.

10. The method of claim 1 wherein the pressure cook vessel includes an extruder mechanism whereby the citrus peels are further ground into smaller particle sizes while being heated under elevated pressure.

11. The method of claim 1 comprising the steps of transferring the heated citrus peels of the citrus peel slurry from the pressure cook vessel to a first centrifuge and mixing the heated citrus peels with water to separate into peel solids and soluble pectin.

12. The method of claim 11 comprising the steps of transferring the peel solids to a second centrifuge and mixing with water for additional dewatering and pectin recovery.

13. The method of claim 11 comprising the step of transferring from the first centrifuge to an evaporator to produce a more concentrated pectin solution.

14. The method of claim 13 comprising the step of routing the concentrated pectin solution to a precipitation unit where it is mixed with a precipitating agent to precipitate pectin from the concentrated solution.

15. The method of claim 1 wherein 8% pectin solution is recovered.

* * * * *